US010004475B2

(12) United States Patent
Quearry (10) Patent No.: US 10,004,475 B2
(45) Date of Patent: Jun. 26, 2018

(54) ECHOGENIC SURFACES WITH PRESSED-DIMPLE FORMATIONS

(71) Applicant: Muffin Incorporated, West Lafayette, IN (US)

(72) Inventor: Benjaman B. Quearry, Bloomington, IN (US)

(73) Assignee: Muffin Incorporated, West Lafayette, IN (US)

( * ) Notice: Subject to any disclaimer, the term of this patent is extended or adjusted under 35 U.S.C. 154(b) by 457 days.

(21) Appl. No.: 14/199,028

(22) Filed: Mar. 6, 2014

(65) Prior Publication Data

US 2014/0265024 A1 Sep. 18, 2014

Related U.S. Application Data

(60) Provisional application No. 61/783,043, filed on Mar. 14, 2013, provisional application No. 61/782,890, filed on Mar. 14, 2013.

(51) Int. Cl.
*B29C 59/04* (2006.01)
*A61B 8/00* (2006.01)
(Continued)

(52) U.S. Cl.
CPC .......... *A61B 8/4455* (2013.01); *A61B 8/0841* (2013.01); *A61B 17/3421* (2013.01); *A61B 90/39* (2016.02); *A61B 8/4483* (2013.01); *A61B 8/58* (2013.01); *A61B 2017/00526* (2013.01); *A61B 2017/00725* (2013.01); *A61B 2017/3413* (2013.01); *A61B 2090/3925* (2016.02)

(58) Field of Classification Search
CPC . A61B 2090/3925; A61B 8/4263; A61B 8/44; A61B 8/4444; A61B 8/445; A61B 8/4455
See application file for complete search history.

(56) References Cited

U.S. PATENT DOCUMENTS 4,055,167 A 12/1977 Bernstein
4,401,124 A 8/1983 Guess et al.
(Continued)

FOREIGN PATENT DOCUMENTS

DE 2425724 11/1975
DE 20 2009 005 135 U1 8/2009
(Continued)

OTHER PUBLICATIONS

International Search Report and Written Opinion issued in PCT/US2014/021063, dated Jun. 23, 2014.
(Continued)

*Primary Examiner* — Ryan Ochylski
(74) *Attorney, Agent, or Firm* — Woodard, Emhardt, Moriarty, McNett & Henry LLP (57) ABSTRACT

Disclosed are embodiments of methods and devices for providing enhanced echogenicity to medical devices. The method includes rolling an impression roller having a plurality of protrusions and an outer surface against a medical device. The protrusions create depressions in the surface of the medical device. A guide roller forms a ridge of the depression into the depression to create a lobe. The lobe forms a pocket between a bottom surface of the depression and the lobe.

21 Claims, 7 Drawing Sheets

(51) Int. Cl.
  *A61B 8/08* (2006.01)
  *A61B 17/34* (2006.01)
  *A61B 90/00* (2016.01)
  *A61B 8/12* (2006.01)
  *A61B 17/00* (2006.01)

(56) References Cited

U.S. PATENT DOCUMENTS

| | | |
|---|---|---|
| 4,411,657 A | 10/1983 | Galindo |
| 4,490,139 A | 12/1984 | Huizenga et al. |
| 4,566,438 A | 1/1986 | Liese et al. |
| 4,582,061 A | 4/1986 | Fry |
| 4,627,444 A | 12/1986 | Brooker |
| 4,702,260 A | 10/1987 | Wang |
| 4,708,147 A | 11/1987 | Haaga |
| 4,791,937 A | 12/1988 | Wang |
| 4,799,495 A | 1/1989 | Hawkins et al. |
| 4,869,259 A | 9/1989 | Elkins |
| 4,900,300 A | 2/1990 | Lee |
| 4,903,709 A | 2/1990 | Skinner |
| 4,977,897 A | 12/1990 | Hurwitz |
| 4,989,614 A | 2/1991 | Dejter, Jr. et al. |
| 4,991,592 A | 2/1991 | Christ |
| 5,048,530 A | 9/1991 | Hurwitz |
| 5,081,997 A * | 1/1992 | Bosley, Jr. ............. A01K 85/00 424/9.4 |
| 5,106,364 A | 4/1992 | Hayafuji et al. |
| 5,161,542 A | 11/1992 | Palestrant |
| 5,221,269 A | 6/1993 | Miller et al. |
| 5,320,110 A | 6/1994 | Wang |
| 5,383,466 A | 1/1995 | Partika |
| 5,425,376 A | 6/1995 | Banys et al. |
| 5,449,001 A | 9/1995 | Terwilliger |
| 5,458,112 A | 10/1995 | Weaver |
| 5,470,308 A | 11/1995 | Edwards et al. |
| 5,490,521 A | 2/1996 | Davis et al. |
| 5,535,755 A | 7/1996 | Heske |
| 5,553,477 A | 9/1996 | Eisensmith et al. |
| 5,759,154 A | 6/1998 | Hoyns |
| 5,807,304 A | 9/1998 | Cockburn |
| 5,817,033 A | 10/1998 | DeSantis et al. |
| 5,829,439 A | 11/1998 | Yokosawa et al. |
| 5,865,765 A | 2/1999 | Mohajer |
| 5,911,939 A * | 6/1999 | Jenkins ................. B29C 59/043 264/286 |
| 5,934,212 A | 8/1999 | Gitlin et al. |
| 5,967,988 A | 10/1999 | Briscoe et al. |
| 5,971,939 A | 10/1999 | DeSantis et al. |
| 6,053,870 A | 4/2000 | Fulton, III |
| 6,663,592 B2 | 12/2003 | Rhad et al. |
| 6,709,408 B2 | 3/2004 | Fisher |
| 7,258,699 B2 | 8/2007 | Russell |
| D657,461 S | 4/2012 | Schembre et al. |
| 2003/0008073 A1 * | 1/2003 | Godel .................. B21C 37/207 427/287 |
| 2003/0158480 A1 * | 8/2003 | Tornes .................. A61B 19/54 600/437 |
| 2006/0034884 A1 * | 2/2006 | Stenzel .................. A61F 2/86 424/422 |
| 2009/0054773 A1 | 2/2009 | Shizuka |
| 2009/0137906 A1 | 5/2009 | Maruyama et al. |
| 2011/0046619 A1 | 2/2011 | Ducharme |
| 2011/0160592 A1 | 6/2011 | Mitchell |
| 2012/0059250 A1 | 3/2012 | Gray et al. |
| 2012/0117807 A1 | 5/2012 | Maruyama et al. |
| 2012/0253228 A1 | 10/2012 | Schembre et al. |
| 2012/0253297 A1 | 10/2012 | Matsuzawa |
| 2013/0267942 A1 | 10/2013 | Fulton, III |
| 2017/0049993 A1 * | 2/2017 | Cosman ............ A61M 25/0105 |

FOREIGN PATENT DOCUMENTS

| | | |
|---|---|---|
| EP | 0 019 104 A2 | 4/1980 |
| EP | 0 127 781 A2 | 12/1984 |
| EP | 0 624 342 A1 | 11/1994 |
| EP | 1 426 011 A1 | 9/2004 |
| JP | 3171525 | 8/1996 |
| JP | 2010-185472 | 7/1998 |
| JP | H10-185472 A | 7/1998 |
| JP | 2000-051219 A | 2/2000 |
| JP | 2006-271874 | 10/2006 |
| KR | 10-2012-0027340 A | 3/2012 |
| WO | WO 2008/062451 A2 | 5/2008 |
| WO | WO 2012/133276 A1 | 10/2012 |

OTHER PUBLICATIONS

NPL—Abstract of Corresponding Application US2010288706 A1 for KR 10-2012-0027340, Method For Preparing At Least One Compound From Blood, and Sampling Device For Use When Carrying Out Said Method, Biotechnology Institute, Mar. 21, 2012.
NPL—English Translation of Abstract, JP10185472A, Entitled: Manufacture of Heating Tube, Jul. 14, 1998.
PCT/US2014/021063 International Preliminary Report on Patentability.
DE 20 2009 005 1350U1 Machine Translation.
DE 2425724 English Abstract.
EP 0 019 104 A2 English Abstract.
JP 2006-271874 English Astract.
Sviggum et al., "Needle Echogenicity in Sonographically Guided Regional Anesthesia", American Institute of Ultrasound in Medicine, J Ultrasound Med 2013; 32:143-148.
WO 2012/33276 A1 English Abstract.
English Abstract of 2000-051219 A.
English Abstract of 3171525.
English Abstract of H10-185472A.

* cited by examiner

ECHOGENIC SURFACES WITH PRESSED-DIMPLE FORMATIONS

REFERENCE TO RELATED APPLICATIONS

This application claims the benefit of U.S. Provisional Patent Application No. 61/783,043, filed Mar. 14, 2013, and U.S. Provisional Patent Application No. 61/782,890, filed Mar. 14, 2013, which are hereby incorporated by reference in their entireties.

FIELD

The present disclosure concerns devices and methods for ultrasound use within the human body, including devices and methods for enhancing ultrasound visibility.

BACKGROUND

Medical devices for subcutaneous use are known in the medical field. For example, biopsy needles are used to capture and remove internal tissues while avoiding invasive surgery. When performing medical procedures, often targeted bodily areas are surrounded by blood vessels or internal organs which can cause difficulties with accurate percutaneous positioning of medical devices. Imaging methods can mitigate some of these difficulties by providing for simultaneous imaging of internal organs and medical devices. Ultrasound imaging is particularly suitable due to its lesser operation cost and increased portability in comparison to other imaging modalities such as X-ray and MRI. During ultrasound imaging procedures, a transducer emits ultrasound waves. A portion of the ultrasound waves reflect when encountering organs, tissues, and other items inside the body and then return to the transducer. The returned sound waves are then used to produce a visual representation of an internal cavity. This provides a real-time moving image of the internal organs and medical device which a physician can use to guide the medical device to the desired bodily area.

Problems exist with current uses of ultrasound imaging to place a medical device subcutaneously because the image obtained through ultrasound is not always clear. However, there are ways to increase image clarity. Echogenic enhancements in the form of a matrix of depressions (i.e. dimples) in the surface of a medical device can cause an altered or improved reflective response of ultrasound waves. When applied to a medical device, echogenic enhancements can cause the medical device to have greater ultrasound image clarity. This in turn can increase positioning accuracy of the medical device.

Traditional methods of producing depressions on surfaces of medical devices are costly and time-consuming. For example, each reflected depression is commonly formed by using a punch to impact the surface of the medical device in order to create each individual dimple. After each punch strike, the needle is moved to the next point and another punch strike is made. The density of the matrix and, ultimately, the image quality of the device is limited by the number of punch strikes required to generate the matrix. This method is slow and can result in wasted time and costs, such as when a punch breaks and an entire batch of medical devices must be discarded. Other methods for creating a matrix of depressions can be used, such as by a laser ablation, particle (i.e. bead) blasting, or chemical machining. However, these methods are equally slow and offer lower echogenicity compared to punched dimples. Thus, there is a need for a method of producing echogenic enhancements on medical devices which is faster and less wasteful than traditional manufacturing methods, while also providing superior echogenicity.

SUMMARY

Among other things, disclosed is a method and device for providing enhanced echogenicity to a medical device. In one example, a method of adding echogenic features to a medical device includes positioning a roller adjacent to a medical device, wherein the roller has an outer surface including at least one protrusion, wherein the device has a device surface, and rotating the roller with respect to the device so that the at least one protrusion presses into the device surface to form a depression. The method can further include aligning a roller axis of the roller with respect to a device axis of the device. The method can further include aligning a roller axis of the roller at a pitch angle with respect to a device axis of the device, wherein the device axis extends axially through the device and wherein the roller axis extends axially through the roller.

The roller's outer surface can include a plurality of protrusions, and methods can include rotating the roller with respect to the device so that the plurality of protrusions press into the device surface to form a series of depressions arranged helically about the device surface. In some embodiments, methods include the step of the roller applying an axial force to the device which causes the device to move axially. The device can be cylindrical. Method examples can further include the step of creating a ridge around a rim of the depression, wherein the ridge extends above (i.e. is positioned radially further than the radially outward-most extent of) the device surface, which may be a generally cylindrical device surface. The method can further include the step of rotating a guide roller with respect to the device so that the guide roller rolls against the device surface.

Embodiments can further include the step of forming a portion of the ridge into or over the depression to create a lobe extending over the depression, wherein a portion of the lobe faces a bottom surface of the depression. Such a lobe may define a pocket between the bottom surface and the lobe, and wherein the bottom surface is within the rim of the depression and faces outward of the depression. The method can further include the step of forming a lobe in or over the depression, wherein a portion of the lobe faces a bottom surface of the depression, and wherein the lobe defines a pocket between the bottom surface and the lobe, and wherein the bottom surface is within a rim of the depression and faces outward of the depression.

The roller can include a plurality of protrusions, wherein at least one of the protrusions is oriented about its central axis at an angle that is different from the angle of an adjacent protrusion. Such protrusions, wherein at least one of the protrusions has a major dimension that is different from the major dimension of an adjacent protrusion. The roller can include a plurality of protrusions, wherein at least one of the protrusions has a height that is different from the height of an adjacent protrusion.

In particular examples, the at least one protrusion can have three protrusion surfaces, wherein each protrusion surface intersects the other protrusion surfaces, and wherein each protrusion surface is concave toward the center of the protrusion. The at least one protrusion can have three protrusion surfaces, wherein each protrusion surface intersects the other protrusion surfaces, and wherein at least one protrusion surface has a dimension aligned with the device surface that is different from a dimension aligned with the device surface of another protrusion surface.

An apparatus for providing echogenic features to a medical device can include an impression roller and a guide roller positioned to contact a medical device positioned therebetween, wherein the impression roller includes an outer surface, wherein the impression roller includes a plurality of protrusions located in the outer surface, and wherein the protrusions extend radially further than the radially outermost extent of the outer surface. The apparatus can operate such that during operation the impression roller rotates about its center axis, and wherein the protrusions impact a surface of the medical device and create depressions in the surface of the medical device. The apparatus can operate such that during operation the protrusions create a ridge around a rim of the depressions and wherein the guide roller presses a portion of the ridge into the depression creating a lobe.

Further forms, objects, features, aspects, benefits, advantages, and embodiments of the present disclosure will become apparent from a detailed description and drawings provided herewith.

DESCRIPTION OF THE ILLUSTRATED EMBODIMENTS

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates. Embodiments are shown in detail; although it will be apparent to those skilled in the relevant art that some features that are not relevant to the present disclosure may not be shown for the sake of clarity.

Disclosed herein are embodiments of an apparatus and method for production and/or modification of medical devices 20 (FIG. 1) which are suitable for endoluminal medical procedures. In some embodiments an apparatus includes one or more rollers having surface projections. When rolled against device 20 (e.g. a blank or other workpiece) under certain circumstances, the surface projections create a matrix of depressions in a surface of device 20. The matrix of depressions form an area of device 20 which is echogenically enhanced, making device 20 particularly suitable for use in conjunction with an ultrasound system. The depressions include surface features which enhance, scatter, and/or redirect ultrasound signals.

In some cases, device 20 is used with a system that includes an ultrasound console (not shown) to provide imaging of device 20. The console portion can be connected to commercially available ultrasound probes or transducers with compatible pinout, or other medical devices which are configured for endoluminal procedures. The console is configured to process data obtained from an ultrasound transducer, e.g. from signals reflected or otherwise attenuated by device 20, and to create image(s) viewable on a display or other data output.

As used herein, the term "echogenic" describes the characteristic ability of a surface or device to direct a relatively favorable quality and quantity of an ultrasound signal back to a transducer for imaging purposes in comparison to a surface or device (or portion thereof) which is less echogenic, non-echogenic, or echolucent. In other words, a device or surface with increased echogenicity (or greater echogenic response) provides enhanced ultrasound imaging capabilities compared to a device or surface which is relatively less echogenic or more echolucent. As used herein, "echogenicity" typically refers to characteristics of device 20 when device 20 is positioned within a body conduit or other such environment where fluids and/or body tissues surround device 20.

Figure 1:
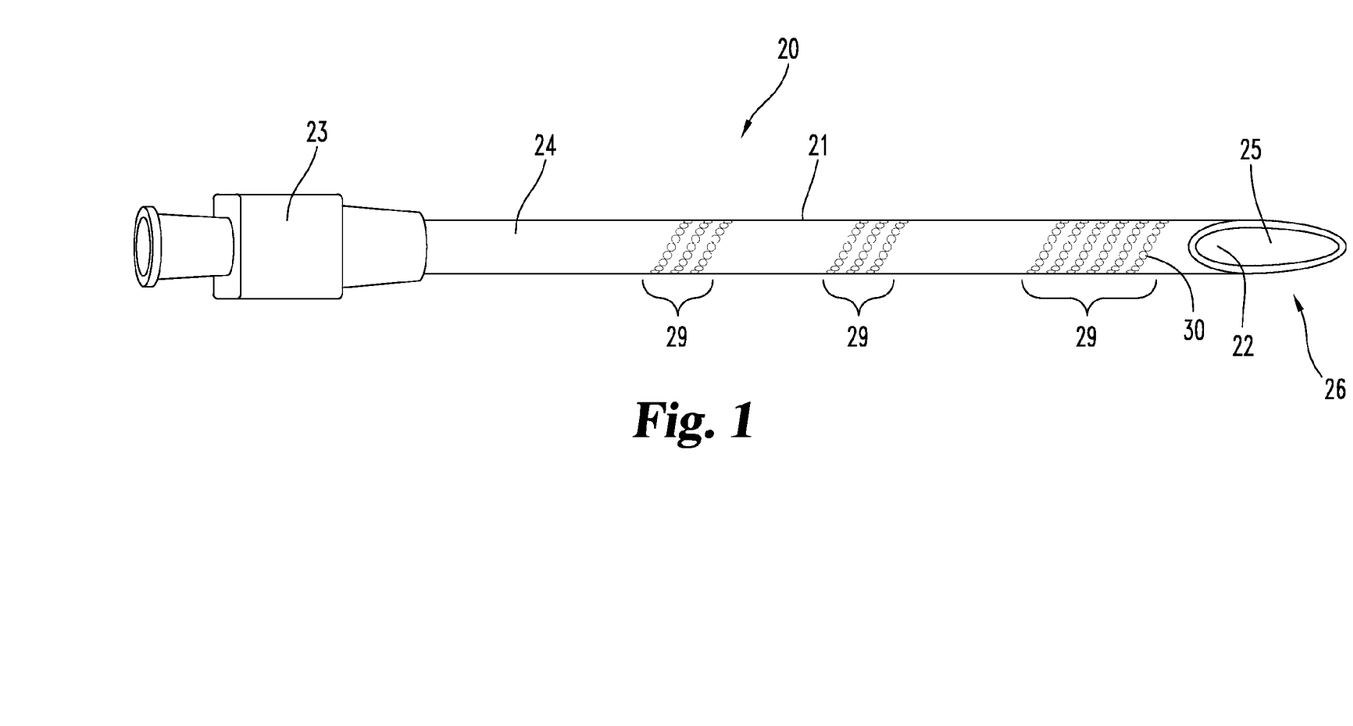
FIG. 1 is a top view of a medical device having echogenic regions.

Referring generally to FIG. 1, an embodiment of medical device 20 is illustrated. FIG. 1 shows a perspective view of an exemplary embodiment of device 20 which is in the form of a needle. It should be understood that device 20 could be any of a variety of types of medical devices which are used for percutaneous, subcutaneous or other internal applications involving ultrasound imaging and therapeutic techniques (e.g. biopsy needles, intravascular devices, laparoscopic tools, etc.). Device 20 includes a body 21, a tip 26, and a handle 23. Particular embodiments of device 10 are cylindrical and are sized for insertion into a body without the need for an existing body conduit such as a blood vessel.

Body 21 in the illustrated embodiments is an elongated member, e.g. a tube or cannula having an outer surface 24 (i.e. device surface) and an inner surface 22 defining a lumen 25 (FIG. 2), with surfaces 22 and 24 being cylindrical as an example. Body 21 terminates at tip 26. Body 21 can be constructed of any suitable metal or polymer which is biocompatible and otherwise structurally appropriate for use as described herein.

Device 20 includes a control end which during use is nearest to the user and an application end which during use is nearest to the user's point of interest. The terms "control" and "application" are used throughout this description to describe these positional orientations. The control end of device 20 may extend outside of the patient during use. Alternatively, the control end may attach to another piece that extends outside the patient. The control end generally ends in a handle 23 or other operating portion for maneuvering device 20. Handle 23 can be any of a variety of forms or structures suitable for use in conjunction with needles or medical devices used in percutaneous applications. Handle 23 is constructed to be manipulatable by hand in some embodiments and has a hollow axis in communication with lumen 25 and which can receive a stylet or other cylindrical objects.

The application side end of body 21 is formed as a beveled tip 26 in some embodiments. The bevel is generally constructed by cutting the cannula along a plane oblique to the lumen axis, i.e. a plane having a normal that is nonparallel to the lumen axis. Other embodiments of body 21 may have alternative configurations. Tip 26 has cutting edges where the angle between the bevel surface and the outer surface is acute. Typically such bevels are capable of piercing or slicing tissue. Although the embodiment of tip 26 described herein is generally a planar cut configuration, other configurations of needle tips with varied cutting edges could be used.

For some applications, it is preferable for device 20 to have one or more echogenic regions (e.g. regions 29) which are populated with a matrix of features 30 that provide enhanced echogenicity to device 20. Features 30 are formed as depressions positioned in surface 24. Features 30 include one or more surfaces and a rim. The rim generally defines the radially outermost extent of the depressions. In other words, the rim is defined by the intersection of the surface of the depressions and surface 24 of device 20. The depressions each have an apex located at the radially inward-most portion of the depressions (or the point of the depression which is radially furthest from the rim). Examples of devices having enhanced echogenicity are described in U.S. Provisional Patent Application Ser. No. 61/782,890, entitled "Echogenic Surface Using Reuleaux Triangle," filed on Mar. 14, 2013, and incorporated herein by reference in its entirety. An apparatus and method as described herein provides an efficient and cost-effective way to add echogenic enhancements to an elongated cannula, such as body 21 or device 20.

Figure 2:
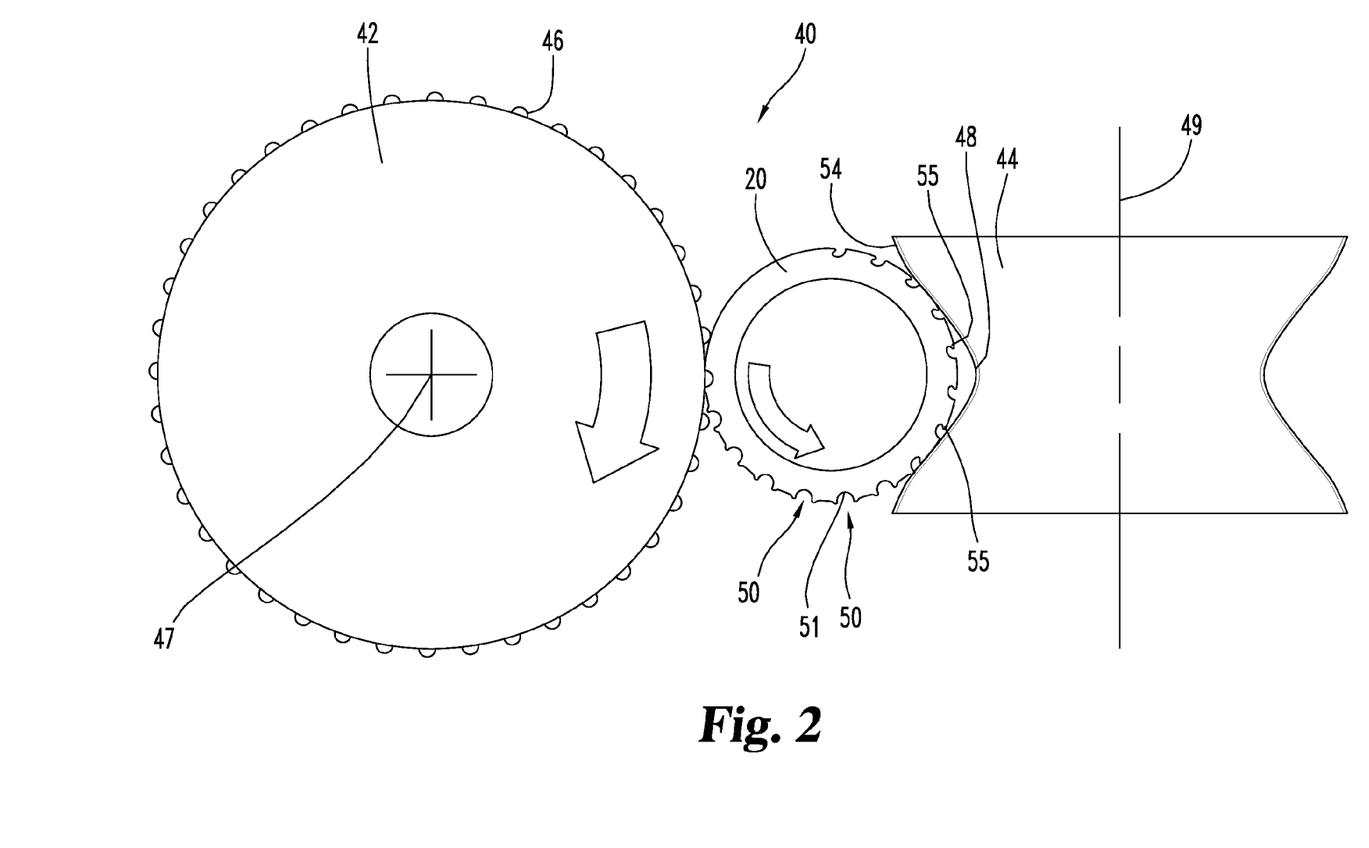
FIG. 2 is an illustrative view of a portion of a roller apparatus having an impression roller, a guide roller, and a cross section of the medical device of FIG. 1.
Figure 3:
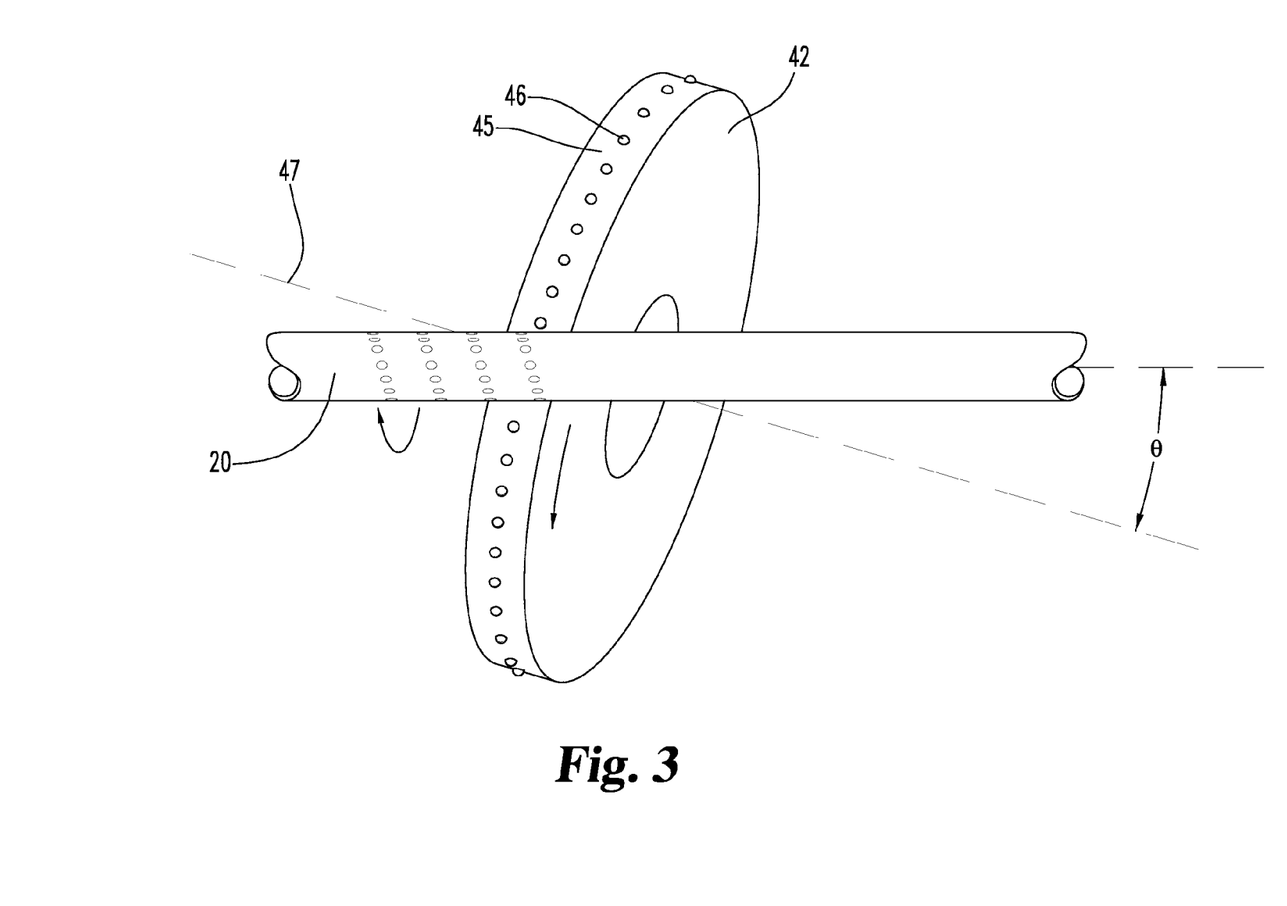
FIG. 3 is an illustrative perspective view of an impression roller and the medical device of FIG. 1.

Referring to FIGS. 2 and 3, disclosed is an apparatus 40 (shown schematically) having an impression roller 42 and a guide roller 44. Impression roller 42 and guide roller 44 are positioned in a structural apparatus (not shown) that provides rotational motion to both rollers 42, 44. Rotational motion can be achieved through axles, bearings, or other suitable structures that allow rollers 42, 44 to rotate about their respective axes. Impression roller 42 and guide roller 44 are arranged to provide a space for device 20 to be positioned therebetween. Impression roller 42 and guide roller 44 are movable relative to each other to accommodate various sizes of device 20 as well as loading and unloading of device 20. The structural apparatus allows device 20 to be rotatably positioned between impression roller 42 and guide roller 44. This is achieved through any suitable means such as shafts, bearings, or a support having a configuration of rollers, for example.

Impression roller 42 is positioned to rotate about a roller axis 47 which extends axially through impression roller 42 (e.g. perpendicular to the page in FIG. 2). In some embodiments, impression roller 42 is positioned so that roller axis 47 is parallel with the axis of device 20. Alternatively, impression roller 42 can be positioned so that roller axis 47 is arranged at a pitch angle θ that is angularly offset from a direction which is parallel with the axis of device 20. Pitch angle θ can vary between 0° and about 7°. As can be seen in FIG. 3, the pitch angle is generally based on the diameter of device 20 and the desired density of the echogenic region using the following formula: arctan(axial spacing of the matrix of depressions/(Pi*device 20 diameter)). Impression roller 42 has a motor or other suitable mechanism which is capable of causing impression roller 42 to rotate about roller axis 47.

Impression roller 42 has a plurality of projections 46 arranged on its outer surface 45, which is cylindrical in the illustrated embodiment. Projections 46 extend radially further than the outermost extent of surface 45. Projections 46 are generally constructed of a material having high hardness. In particular, projections 46 have hardness greater than the hardness of the material of body 21, so that projections 46 are capable of forming an impression (or depression) in surface 24 of device 20. In certain embodiments, projections 46 are formed in a variety of shapes and arranged in a variety of arrangements, as discussed below.

Guide roller 44 is positioned to abut against device 20 during operation. Guide roller 44 is in the general shape of a disc in this embodiment, with an outer rim surface 54 with a general V-shape having apex 48 at the center of the V. The V-shape is configured to support and guide device 20 in certain embodiments. Guide roller 44 can be moved between various positions so that it is rotatable about axes which are perpendicular to one another. In the illustrated example (FIG. 2), guide roller 44 is positioned to rotate about a guide axis 49 which is perpendicular to the axis of device 20. In other examples, guide roller 44 can be moved into position in which guide axis 49 is parallel to the axis of device 20. Alternatively, guide roller 44 can be moved into a position in which guide axis 49 is parallel to the roller axis 47. In some embodiments, guide roller 44 has a motor or other suitable mechanism which is capable of causing guide roller 44 to rotate about guide axis 49.

Apparatus 40 provides the structure and capability to add features 30 to surface 24. During use, device 20 is positioned between impression roller 42 and guide roller 44 in apparatus 40. Impression roller 42 is positioned at pitch angle θ relative to the axis of device 20 as described previously. Impression roller 42 is brought against device 20 and guide roller 44 is brought against device 20 opposite to impression roller 42. A suitable force is applied to device 20 by impression roller 42 and guide roller 44. Impression roller 42 and/or guide roller 44 is caused to rotate. Such rotation causes device 20 to also rotate. As impression roller 42 rotates, projections 46 sequentially impact surface 24. The proximity of impression roller 42 and guide roller 44 cause impression roller 42 to impact device 20 with sufficient force for projections 46 to push into and deform surface 24, thereby creating features 30 in the form of depressions 50 (FIG. 2). Simultaneously, the torque force of transmission roller 42 is transmitted to device 20 causing device 20 to rotate. At the same time, pitch angle θ causes the torque force to transmit an axial force component to device 20, which causes device 20 to move axially. The combined rotation and axial movement of device 20 creates a sequence of features 30 in the form of a helical pattern on surface 24.

Depressions 50 are voids or holes in the surface of 24. Depressions 50 have a lower or inner depression surface 51 (FIGS. 4 and 5) which is generally positioned radially inward of the radially outermost extent of surface 24. Depressions 50 have a ridge 52 which has a surface generally continuous with depression surface 51. Ridge 52 extends radially outward of the radially outermost extent of surface 24. Ridge 52 is formed from elastic deformation and displacement of the material of device 20 due to the creation of depression 50.

As impression roller 42 rotates, projections 46 impact and deform surface 24 as described previously. The impact and deformation process causes device 20 to rotate about its axis in response to rotation of impression roller 42. Device 20 rotates at a rate such that surface 24 moves with a linear speed substantially similar to the linear speed of surface 45. As device 20 rotates, depressions 50 move away from impression roller 42 and towards guide roller 44 (i.e. counterclockwise in the FIG. 2 embodiment).

As device 20 rotates further, surface 24 engages surface 54 of guide roller 44. In some embodiments, surface 54 is formed from a compliant polymer material in which case depressions 50 remain substantially unchanged as depressions 50 rotate through and abut against guide roller 44 (not shown). In the arrangement shown in FIG. 2 with guide axis 49 being perpendicular to device axis 20, surface 24 of device 20 slides along surface 54. The sliding engagement can be assisted through use of suitable lubricants or through the use of a compliant polymer material having a low kinetic friction coefficient. The arrangement shown in FIG. 2 is particularly suitable for smaller diameter cannulas (e.g. 26 gauge needles having 0.022 inch diameter), as the V-shape of surface 54 assists in maintaining device 20 in a desired position. In this embodiment, guide roller 44 provides a driving rotation to cause device 20 to move axially simultaneously while rotating. Such motion is in conjunction with or in place of the axial motion created by impression roller 42, and is particularly helpful to provide a helical arrangement, as previously described. In other embodiments (not shown) guide roller 44 is arranged with guide axis 49 positioned parallel with the axis of device 20 or with the roller axis 47. In that embodiment, surface 54 of guide roller 44 engages surface 24 and in some embodiments provides driving rotation to device 20 or rotates along with device 20. In some embodiments, surface 54 can be altered or replaced with a surface not having the V-shape to provide greater contact between surface 54 and surface 24. This arrangement is particularly suitable for larger diameter cannulas (e.g. 6 gauge needles having 0.202 inch diameter). Guide roller 44 applies a positive pressure to device 20, and may do so at all times that device 20 is between rollers 42 and 44.

In some embodiments, guide roller 44 is configured to further deform surface 24 and/or depressions 50 (see FIG. 2). In that case, surface 54 of guide roller 44 is formed from a hard material which has a hardness that is greater than the material of device 20, such as hardened steel. In some embodiments, the pressure applied between guide roller 44 and device 20 is increased compared to embodiments in which surface 54 is formed from a compliant material. As device 20 rolls against surface 54, surface 54 presses against ridge 52 and pushes or bends a portion of ridge 52 into or over depression 50. This creates a lobe 55 (see FIGS. 4 and 5). Lobe 55 is generally the portion of ridge 52 which is pressed toward or into depression 50. The remaining portion of ridge 52 is pushed into surface 24 through elastic deformation of the material of device 20. This process tailors surface 24 in such a way to leave little or no material extending radially further than the radially outermost extent of surface 24.

Figure 4:
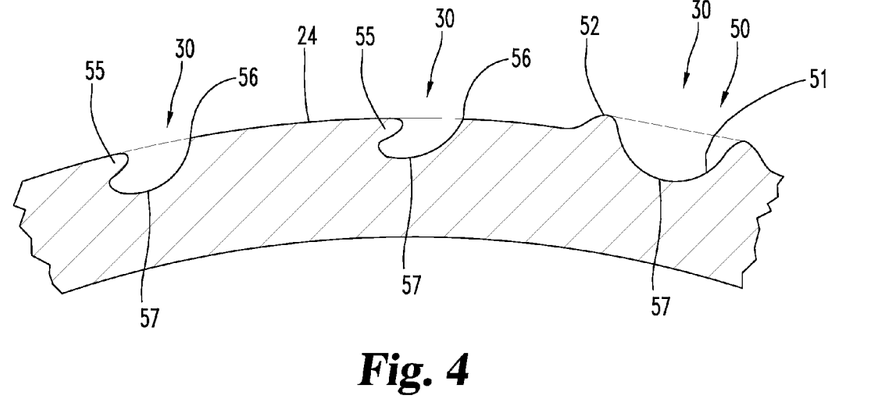
FIG. 4 is a cross section view of a portion of an embodiment of the medical device of FIG. 2.
Figure 5:
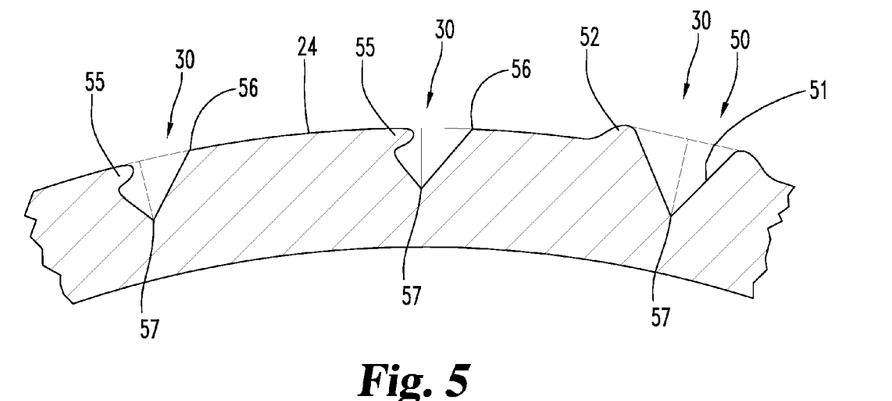
FIG. 5 is a cross section view of a portion of an embodiment of the medical device of FIG. 2.

In this way, features 30 can be varied by adding lobe 55 which extends over a portion of the depression (see FIGS. 4 and 5). Lobe 55 is generally a feature which is added to an echogenic feature 30 as already described. Lobe 55 is formed from the material of device 20 in this example, and generally extends from or between one or more edges of a rim 56 and over a portion of the depression. Rim 56 as previously described, is generally that portion of feature 30 in which the depression surface 51 intersects surface 24, or where it would intersect surface 24 in the absence of lobe 55. Lobe 55 generally extends over less than half of the depression, although in some embodiments lobe 55 extends over more than half of the depression. In other words, lobe 55 generally extends from about less than half of the length of rim 56. Lobe 55 defines a pocket between it and a bottom portion of depression surface 51 (i.e. bottom surface). The bottom portion of depression surface 51 is generally a portion of depression surface 51 which occupies the radially inward-most extent of depression 50, or the portion having an apex 57. The bottom portion faces outward of depression 50 through the area defined by rim 56, or that area which would be defined by rim 56 in absence of lobe 55.

As apparatus 40 operates, a series of depressions 50 are created in surface 24. Pitch angle $\theta$ of impression roller 42 causes depressions 50 to be arranged in a helical pattern around the circumference of surface 24. Similarly, pitch angle $\theta$ of impression roller 42 causes impression roller 42 to create a force component acting upon device 20 in its axial direction, which causes device 20 to move axially within apparatus 40. The axial force component from impression roller 42 can function instead of or in conjunction with any axial force created by guide roller 44. The helical pattern of the echogenic regions allows for greater visibility around the circumference of device 20. This allows the physician to maintain the location of device 20 across a wider range of needle insertion angles, transducer angles, and depths of insertion.

Pitch angle $\theta$ can be varied in order to control the density of the populations of features 30. Lower pitch angles generally provide greater densities while higher pitch angles generally provide lower densities. Greater densities provide stronger echogenic response in some cases, such as, for example a helical configuration with tighter coils. Lesser densities provide less echogenic response in some cases, such as, for example, a helical configuration with looser coils. Pitch angle $\theta$ can also be varied according to the size of device 20, with lower pitch angles (i.e. 1°) corresponding with the largest needles and higher pitch angles (i.e. 7°) corresponding to the smallest needles.

Apparatus 40 provides a way to create echogenic features that is significantly faster and more cost efficient than existing methods. For example, existing methods (i.e. the punch method) can produce echogenic features at a maximum of 60 features per second. Further, the punch method cannot create lobes 55 which prove particularly advantageous for both increasing echogenicity and decreasing discomfort. In contrast to existing methods, roller method disclosed herein can operate at relatively high speed which reduces manufacturing time while increasing matrix density and improving echogenicity. Apparatuses using the roll method are capable of creating echogenic features at a rate of at least 2000 features per second while simultaneously creating echogenic features having lobes 55.

The pocket created by lobe 55 can be used to trap air, $CO_2$, contrast agent, bodily fluid or other material. Upon insertion of device 20, the bubble created in the pocket causes scattering of ultrasound signals so that at least a portion of an ultrasound signal is directed back to towards the transducer. This works in conjunction with the reflective capability of surfaces 51 to greatly improve the echogenicity of device 20.

In various embodiments, certain characteristics of features 30 are varied in order to increase or modify the echogenic response, particularly across a range of frequencies and spatial orientations between an ultrasound transducer and device 20. Variations to the structure and arrangement of features 30 are generally made by tailoring and/or modifying certain aspects of projections 46 on impression roller 42. Certain variations include variations in the dimensions and shapes of features 30, variations in the angular orientation of depressions 50 relative to each other, and populations of features 30 having a mixture of the variations of all of the above.

Figure 6:
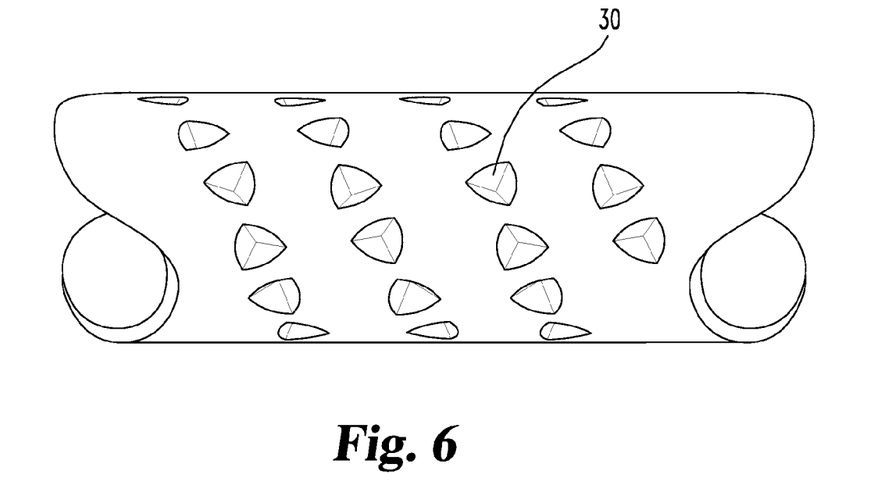
FIG. 6 is a partial perspective view of an embodiment of a medical device having echogenic features with varied angular orientations.
Figure 7:
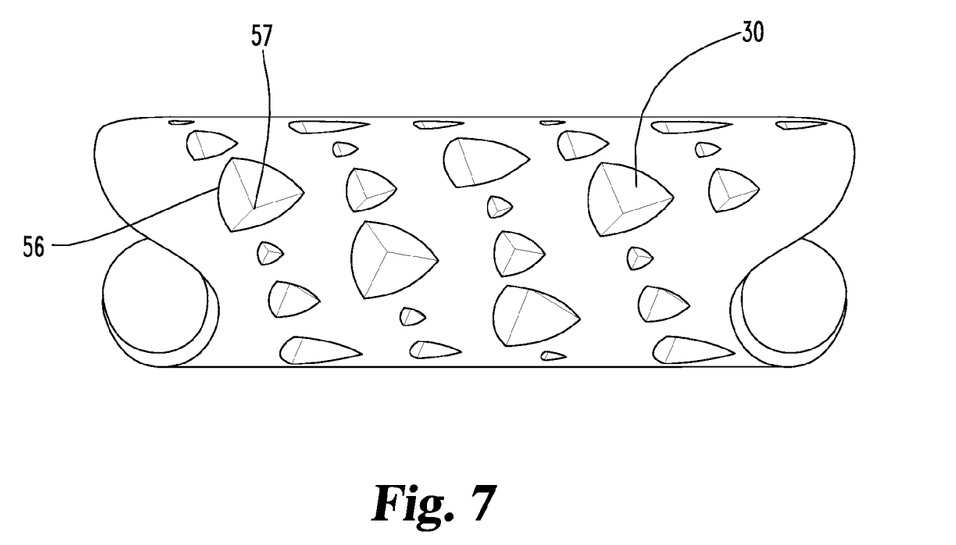
FIG. 7 is a partial perspective view of an embodiment of a medical device having echogenic features with varied major dimensions.

As a specific example, the embodiment shown in FIGS. 5, 6, and 7 has feature 30 with three curved surfaces. Each surface intersects the other two surfaces. The surfaces extend between apex 57 and rim 56. Rim 56 generally represents the intersection of features 30 with surface 24. All three surfaces converge at apex 57. In that way, each feature 30 is constructed in a somewhat inverse pyramidal shape having curved surfaces and a central axis extending through apex 57. Each feature 30 has a profile at its rim 56 in the shape of a reuleaux triangle. Rim 56 has three points which are equidistant to one another and three arcs extending between the three points. The three arcs are circular arcs with each having a radius equal to the distance between any two of the points. The reuleaux triangle profile is maintained throughout feature 30 such that a cross section taken generally parallel to rim 56 (or normal to the central axis) at any location between rim 56 and apex 57 has a similar reuleaux triangle profile. In that way, the three surfaces of feature 30 are turned inward or concave toward a center axis. In other words, in this embodiment, feature 30 takes the shape of the union of three cones, with each cone having an axis that intersects one of the points 35 as well as both axes of the other two cones.

Figure 8:
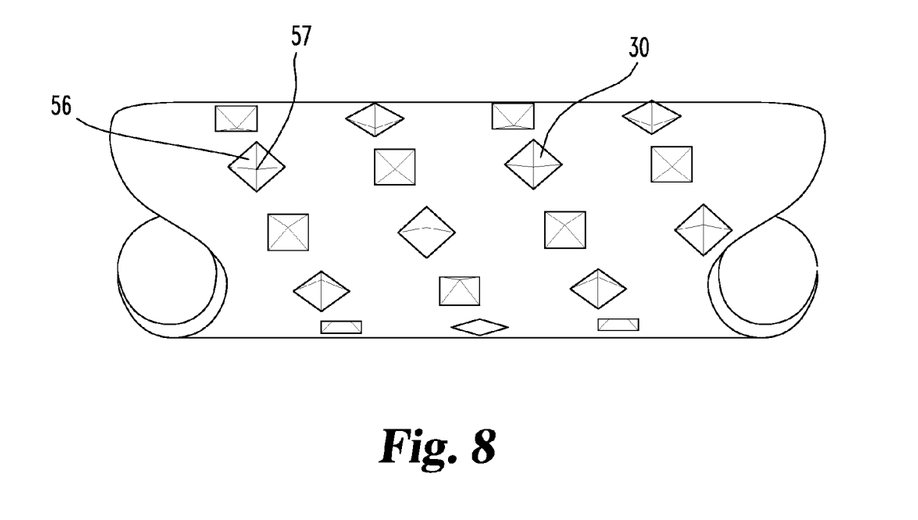
FIG. 8 is a partial perspective view of an embodiment of a medical device having echogenic features with varied angular orientations.
Figure 10:
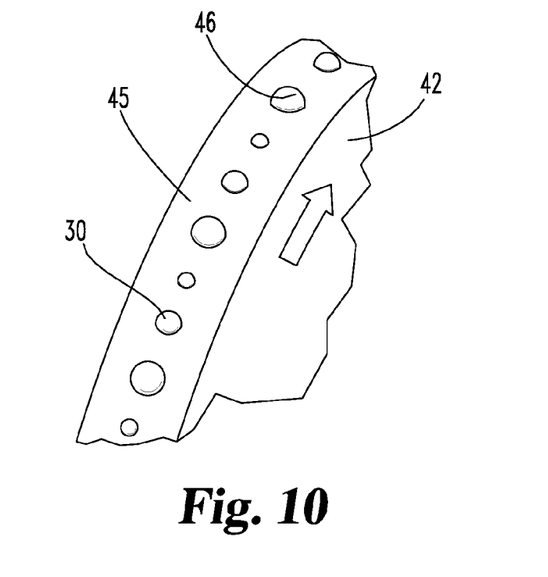
FIG. 10 is a partial perspective view of a portion of an impression roller having protrusions with varied major dimensions.
Figure 11:
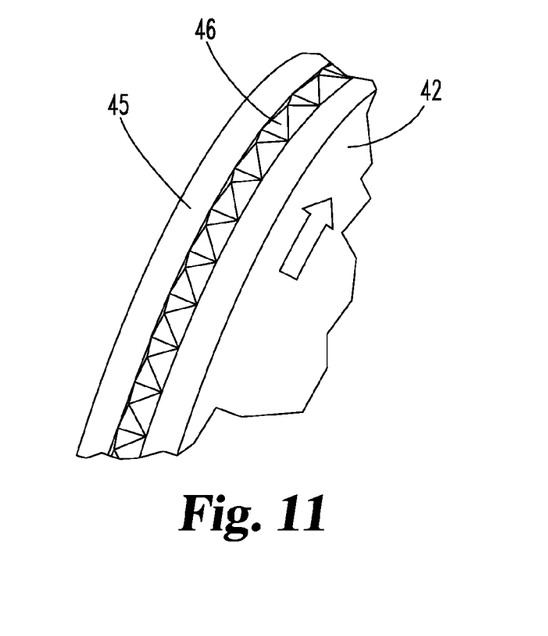
FIG. 11 is a partial perspective view of a portion of an impression roller having protrusions adjacent to one another.

As another example, feature 30 is formed in the shape of a four-sided pyramid, with a square-shaped rim 56 and an apex 57 (see FIGS. 8 and 11). FIG. 11 shows a portion of impression roller 42 having projections 46 in the shape of a four-sided pyramid. Other embodiments of feature 30 can include a hemispherical shape, which when viewed at a cross section resemble truncated half-hemispheres with flat bottomed or round bottomed surfaces (e.g. FIGS. 9 and 10). Other shapes can include tri-corner shapes or hexagons. FIG. 10 shows a portion of impression roller 42 having projections 46 in the shape of half-hemispheres with round bottomed surfaces. Features 30 can be any of a variety of geometric configurations such as, for example, small cavities that are machined into outer surface 24, dimples, divots, grooves, lines, or ridges. Features 30 can be individually located in the cannula wall such that they are not in communication with each other or do not touch each other and are simply a series of individual geometric configurations (e.g. FIG. 10). Alternatively, features 30 could be positioned in outer surface 24 as a continuous texture making the echogenic region substantially occupied by features 30 (e.g. FIG. 11).

Features 30 can be organized and positioned in a variety of configurations. The echogenic region(s) can be formed at any point between the application side end of device 20 and the control side end of device 20. The echogenic region can occupy a portion or all of tip 26, a region adjacent to tip 26, or other parts of device 20. In the embodiment of FIGS. 1 and 2, an echogenic region is positioned near tip 26 so that not only can device 20 be located during ultrasound procedures but also tip 26 can be more accurately positioned during ultrasound procedures. In some embodiments, one or more echogenic regions are also positioned further from tip 26, and can be spaced a known distance apart to provide information to a user during ultrasound procedures, such as the distance of insertion of the needle or the proximity of the tip to certain body tissues (e.g. FIG. 1).

As previously discussed, features 30 are generally arranged in a helical arrangement within the echogenic regions, with each feature 30 being placed along a line representing a helical band about surface 24. In other embodiments, features 30 can be arranged in circumferentially, for example when pitch angle θ is set at 0°.

Particular characteristics of features 30 are varied within echogenic regions (i.e. matrices or populations of features 30) in order to provide enhanced echogenic responses across a range of ultrasound frequencies as well as relative angular orientations between the transducer and device 20. Examples are shown in FIGS. 6-11.

Figure 9:
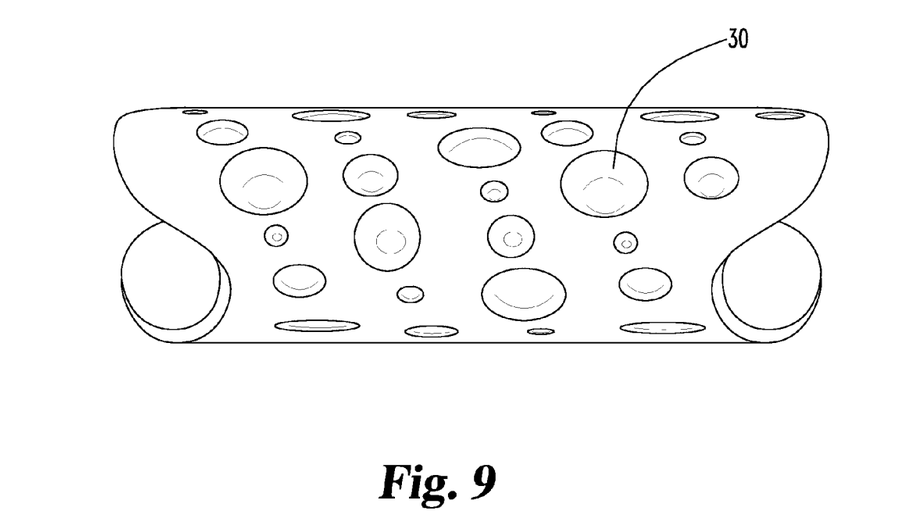
FIG. 9 is a partial perspective view of an embodiment of a medical device having echogenic features with varied major dimensions.

In certain embodiments, the dimensions or characteristics of features 30 are varied, and examples are shown in embodiments of FIGS. 7, 9, and 10. Variations include depressions 50 having varied shapes, variations to the size of the rim, variations to the depth of depressions 50 (i.e. the distance between apex 57 and rim 56), and variations to the angle of surfaces 51 of depressions 50 relative to each other. Each feature 30 has a major dimension which is generally a diameter of a circular area occupied by the rim of each feature 30. In some embodiments, features 30 are formed with three different rim sizes, with each rim size having a different major dimension (e.g. with radii of 0.001 inches, 0.002 inches, and 0.003 inches). The rim sizes alternate in sequence within each helical band, with the largest size being positioned between a small size and a medium size, and the medium size being positioned between a large size and a small size. In other embodiments, more or less rim sizes can be used.

In other embodiments, the depth of features 30 varies over a set range. This variance can extend even to features 30 having the same rim size. Similarly, the relative angles between surfaces 51 of features 30 can vary. In embodiments having features 30 shaped as a reuleaux triangle, two of the three dimensions (rim size, depth, and wall angle) can be varied with the third variable being defined by the other two variables. In other embodiments, many of the dimensions can be varied such as the rim size, depth, surface (or wall) angles, the shape of the rim, and the location of apex 57 relative to rim 56. In embodiments having features 30 with hemispherical shapes, the depth and diameter of the rim can both be varied. Particular embodiments include any number of differently dimensioned features 30. For example, device 20 could include as many as 10, 20, or 50 uniquely dimensioned features 30.

In particular embodiments, features 30 are arranged with different angular orientations relative to one another, as shown in the embodiments of FIGS. 6 and 8. In other words, features 30 can be arranged with a sequential angular rotation value. For example, in the embodiment of FIGS. 6 and 8, features 30 are alternatingly rotated 180° along the helical band. In other embodiments, sequential angular rotations can have a different value (e.g. 30°). In some embodiments, the sequential angular rotation values are randomly chosen and dispersed throughout the population of features 30. In some embodiments, features 30 are configured and arranged with a combination of variance in both dimensions and angular orientations.

In certain embodiments, differently shaped features 30 are combined to co-populate device 20 and/or the echogenic regions. As examples, features 30 having a reuleaux triangle profile can be interspersed with features 30 having a hemispherical shape or features 30 having a square profile can be interspersed with echogenic features having a reuleaux triangle profile. In other embodiments, different profiles of features 30 with each having different dimensions and/or angular orientations relative to one another are placed within a particular helical band.

Features 30 can be further varied by adding lobes 55 as described previously. Features 30 provide device 20 with enhanced echogenic properties. Use of such echogenic features enhances echogenicity as compared to a smooth surface for a similar object. Device 20 having features 30 with dimensions and angular orientations is capable of providing enhanced ultrasound visualization throughout a wide range of ultrasound frequencies and relative angles between device 20 and the transducer.

Certain embodiments of device 20 as described herein were tested using a test fixture which was designed to produce quantifiable data related to ultrasonic visibility of medical devices such as device 20. The test fixture provides quantifiable echogenicity data about medical devices by holding the device and transducer at known and repeatable angles to gather image data for the measurement of echogenicity. The test data obtained illustrates the advantages of the embodiments of device 20 as described herein, particularly when data is compared between device 20 and currently-used medical needles. For example, a device 20 having features 30 in the form of reuleaux triangles arranged with a variation in angular orientation was tested using the test fixture and method described in U.S. Provisional Patent Application Ser. No. 61/782,890, entitled "Echogenic Surface Using Reuleaux Triangle," filed on Mar. 14, 2013, and compared to an existing needle having hemispherical dimples created from a punch method. Device 20 produced a mean brightness rating of 72502 with a standard deviation of 34176, which is a particularly good result compared to existing needle products, which had a mean brightness rating of 33925 with a standard deviation of 23465. An even better result was achieved with an embodiment of device 20 produced through the rolling method and having lobes 55. That embodiment of device 20 included features 30 in the form of reuleaux triangles with lobes 55 and arrangement with variations in angular orientation. That embodiment produced a mean brightness rating of 87440 with a standard deviation of 48648, which is significantly improved relative to existing needle products.

Generally, an ultrasound signal is partially reflected at the interface of two mediums having differing acoustic impedances, such as a fluid and the surface of device 20. The reflected ultrasound signal is enhanced by providing device 20 with features 30 that are more effective at reflecting the ultrasound signal at its particular frequency. Testing results show that the reflective capabilities of such echogenic features are dependent on the dimensions of the features as well as the wavelength of the ultrasound signal. For example, when the major dimensions of features 30 are small compared to the wavelength of the signal, the ultrasound signal becomes diffuse upon interacting with the feature 30 and only a small portion of the signal is reflected back to the transducer. This is similar to fluid waves encountering a wall or feature which is small in comparison to the wavelength. In such circumstances, generally the waves collide and conflict with one another, resulting in overall dampening of the wave.

By incorporating features 30 which have varied dimensions, device 20 can be more effectively imaged using a variety of frequencies of ultrasound, as well as by multiple-frequency ultrasound transducers. For example, device 20 having features 30 with different dimensions and/or characteristics can effectively reflect (for imaging purposes) ultrasound signals having frequencies in the range of 1-20 MHz. Higher frequency ultrasound signals correspond with smaller dimensions, and lower frequency ultrasound signals correspond with larger dimensions. As an example, features 30 having a major dimension of 0.003 inches correspond with and most effectively reflect ultrasound signals having a frequency of 5 MHz. Because a specific ultrasound frequency reflects best from specifically dimensioned features 30, multiple sizes of features 30 allow device 20 to be imaged equally well at a variety of frequencies. In this way, a single device 20 can produce an enhanced ultrasound signal in conjunction with ultrasound transducers and ultrasound imaging equipment for a range of ultrasound frequencies.

Additional testing was performed in an attempt to determine the effects of various echogenic enhancements on the level of discomfort produced by a needle from insertion within a body. Testing was performed by measuring the insertion force of certain embodiments of device 20 and comparing to the measurements for various existing needles. The insertion force generally correlates with the level of discomfort. Although insertion force varies according to the amount of insertion, comparisons were made between the insertion forces at standardized depths among all of the tested medical devices. It was determined that embodiments of device 20 having features 30 in the shape of a reuleaux triangle, manufactured with the roller method described herein, and including lobes 55 require significantly less insertion force compared to other types of needles. For example, such a device 20 has a load value of 0.270 N compared to 0.906 N required by a similar device 20 that does not include lobes 55. As mentioned previously, the surfaces 24 of devices 20 having lobes 55 and no ridge exhibit lower static and kinetic friction coefficients compared to devices 20 that have a ridge and do not have lobes 55.

In practice, due to manufacturing realities the actual shape of features 30 vary somewhat from the theoretical shapes described herein. In some cases, the tools used to create the depressions change shape slightly between the beginning and the end of their service life, which causes some variance in the actual shape of the depressions. In other cases, the materials of device 20 may have granular peculiarities or other characteristics which cause some of the features 30 to have a slightly different shape than the theoretical perfect shape. For example, features 30 created in the reuleaux triangle configuration described previously may not all have a single distinct point representing apex 57. However, it should be understood that features 30 operate as described herein even with slight variances in manufacturing.

While some of the above discussion concerned specific use in the context of ultrasound system applications, it will be understood that embodiments of device 20 could also be used for a variety of other medical procedures and with a variety of other medical devices.

Although particular materials were highlighted herein for some components of device 20, those materials are not intended to be limiting of the types of materials which are suitable to be used in device 20. Additionally, where materials were not highlighted, a variety of materials could be used such as certain types of metals, polymers, ceramics or other types of materials which are suitable for use in devices for small body cavity applications.

While the embodiments have been illustrated and described in detail in the drawings and foregoing description, the same is to be considered as illustrative and not restrictive in character, it being understood that all changes, equivalents, and modifications that come within the spirit of the claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A method of adding echogenic features to a medical device comprising:
    positioning a roller adjacent to a medical device, wherein the roller has an outer surface including at least one protrusion, wherein the device has a device surface;
    rotating the roller with respect to the device so that the at least one protrusion presses into the device surface to form a depression; and
    forming a lobe in the depression, wherein a portion of the lobe faces a bottom surface of the depression, and wherein the lobe defines a pocket between the bottom surface and the lobe, and wherein the bottom surface is within a rim of the depression and faces outward of the depression.

2. The method of claim 1, further comprising:
    aligning a roller axis of the roller at a pitch angle with respect to a device axis of the device, wherein the device axis extends axially through the device and wherein the roller axis extends axially through the roller.

3. The method of claim 1, wherein the outer surface includes a plurality of protrusions, further comprising rotating the roller with respect to the device so that the plurality of protrusions press into the device surface to form a series of depressions arranged helically about the device surface.

4. The method of claim 3, wherein the roller applies an axial force to the device which causes the device to move axially.

5. The method of claim 4, wherein the device is cylindrical.

6. The method of claim 1, wherein forming a lobe in the depression includes creating a ridge around a rim of the depression, wherein the ridge is positioned radially further than the radially outward-most extent of the device surface and presses a portion of the ridge into the depression to create a lobe extending over the depression.

7. The method of claim 6, wherein the forming a portion of the ridge into the depression includes rotating a guide roller with respect to the device so that the guide roller rolls against the device surface and presses a portion of the ridge into the depression.

8. The method of claim 1, wherein the roller further comprises a plurality of protrusions, wherein at least one of the protrusions is oriented about its central axis at an angle that is different from the angle of an adjacent protrusion.

9. The method of claim 1, wherein the roller further comprises a plurality of protrusions, wherein at least one of the protrusions has a major dimension that is different from the major dimension of an adjacent protrusion.

10. The method of claim 1, wherein the roller further comprises a plurality of protrusions, wherein at least one of the protrusions has a height that is different from the height of an adjacent protrusion.

11. The method of claim 1, wherein at least one protrusion has three protrusion surfaces, wherein each protrusion surface intersects the other protrusion surfaces, and wherein each protrusion surface is concave toward the center of the protrusion.

12. The method of claim 1, wherein at least one protrusion has three protrusion surfaces, wherein each protrusion surface intersects the other protrusion surfaces, and wherein at least one protrusion surface has a dimension aligned with the device surface that is different from a dimension aligned with the device surface of another protrusion surface.

13. An apparatus for providing echogenic features to a medical device, comprising:
    an impression roller and a guide roller positioned to contact a medical device positioned therebetween, wherein the impression roller includes a center axis and an outer surface, wherein the impression roller includes a plurality of protrusions located in the outer surface, and wherein the protrusions extend radially further than the radially outermost extent of the outer surface;
    wherein the guide roller rotates about a guide axis which is transverse to the center axis of the impression roller.

14. The apparatus of claim 13, wherein during operation the impression roller rotates about its center axis, and wherein the protrusions impact a surface of the medical device to rotate the medical device about a device axis and to translate the device along the device axis so as to create depressions helically around the medical device in the surface of the medical device.

15. The apparatus of claim 14, wherein during operation the protrusions create a ridge around a rim of the depressions and wherein the guide roller presses a portion of the ridge into the depression creating a lobe.

16. The apparatus of claim 13, wherein the guide roller has an outer surface defining a recess arranged to receive the medical device when the medical device is positioned between the impression roller and the guide roller.

17. A method of adding echogenic features to a medical device comprising:
    positioning a medical device between an impression roller and a guide roller, wherein the impression roller has an outer surface including at least one protrusion, wherein the device has a device surface;
    rotating the impression roller with respect to the device so that the at least one protrusion presses into the device surface to form a depression; and
    wherein the impression roller rotates about a roller axis and the guide roller rotates about a guide axis, and wherein the guide axis is non-parallel to the roller axis.

18. The method of claim 17, wherein the at least one protrusion includes a plurality of protrusions and at least one of the protrusions of the plurality of protrusions is oriented about its central axis at an angle that is different from the angle of an adjacent protrusion.

19. The method of claim 17, wherein the at least one protrusion includes a plurality of protrusions and at least one of the protrusions of the plurality of protrusions has a major dimension that is different from the major dimension of an adjacent protrusion.

20. The method of claim 17, wherein the at least one protrusion includes a plurality of protrusions and at least one of the protrusions of the plurality of protrusions has a height that is different from the height of an adjacent protrusion.

21. A method of adding echogenic features to a medical device comprising:
    positioning a medical device between an impression roller and a guide roller, wherein the impression roller has an outer surface including at least one protrusion, wherein the device has a device surface; and
    rotating the impression roller with respect to the device so that the at least one protrusion presses into the device surface to form a depression;

wherein rotating the impression roller causes rotation of the medical device around a medical device axis; and wherein the rotation of the medical device around the medical device axis causes sliding of the device surface of the medical device along a surface of the guide roller.

* * * * *